United States Patent
Huang et al.

(10) Patent No.: US 9,347,924 B2
(45) Date of Patent: May 24, 2016

(54) CRITICAL FLOW IN MOISTURE GENERATION SYSTEM FOR NATURAL GAS

(71) Applicant: General Electric Company, Schenectady, NY (US)

(72) Inventors: Yufeng Huang, Andover, MD (US); Gary Stephen Parece, Belmont, MA (US); John McKinley Poole, Maynard, MA (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 451 days.

(21) Appl. No.: 13/859,777

(22) Filed: Apr. 10, 2013

(65) Prior Publication Data

US 2014/0305193 A1    Oct. 16, 2014

(51) Int. Cl.
*G01N 33/22*    (2006.01)
*G01N 33/00*    (2006.01)

(52) U.S. Cl.
CPC .......... *G01N 33/0004* (2013.01); *G01N 33/225* (2013.01)

(58) Field of Classification Search
CPC .................................................. G01N 33/225
See application file for complete search history.

(56) References Cited

U.S. PATENT DOCUMENTS

| 3,595,443 | A | | 7/1971 | Jones et al. | |
|---|---|---|---|---|---|
| 2,665,748 | A | | 5/1972 | Mator | |
| 4,131,011 | A | * | 12/1978 | Ling | 73/29.01 |
| 6,182,951 | B1 | | 2/2001 | Hallman, Jr. et al. | |
| 2010/0050666 | A1 | * | 3/2010 | Meyer et al. | 62/94 |

* cited by examiner

*Primary Examiner* — Laura Martin
*Assistant Examiner* — Alex Devito
(74) *Attorney, Agent, or Firm* — Cooper Legal Group, LLC

(57) ABSTRACT

A moisture provision and analyzer arrangement includes a conduit for obtaining a sample flow of natural gas, a moisture analyzer, and a bypass flow conduit. A main orifice is in fluid communication within the moisture provision and analyzer arrangement with flow proceeding to the moisture analyzer. A bypass orifice is located along the bypass flow conduit. The main orifice is sized and the flow provided to the moisture analyzer via the main orifice is at a pressure such that the flow provided to the moisture analyzer is at a critical flow condition and the bypass orifice is sized and the bypass flow is provided at a pressure such that the bypass flow is at a critical flow condition. Components in the moisture provision and analyzer arrangement are selected such that the critical flow rate through the main orifice and the critical flow rate through the bypass orifice are equal.

20 Claims, 2 Drawing Sheets

CRITICAL FLOW IN MOISTURE GENERATION SYSTEM FOR NATURAL GAS

BACKGROUND OF THE INVENTION

1. Field of the Invention

The present invention relates to the liquefaction of natural gas, and more particularly, the present invention relates to monitoring moisture within natural gas prior to the natural gas proceeding to liquefaction.

2. Discussion of Prior Art

Various reasons exist for liquefaction (i.e., the process of making liquid) of gases and particularly of natural gas. One example reason for the liquefaction of raw natural gas is the separation/liquefied into different hydrocarbon components. Another example reason for the liquefaction of natural gas is that the liquefaction reduces the volume of a gas by a factor of about 1/600, thereby making it possible to store and transport the liquefied gas in containers of more economical and practical design. In one example, when gas is transported by pipeline from a source/supply to a distant market, it is desirable to operate under a substantially constant high load factor. Often the capacity will exceed demand while at other times the demand may exceed the capacity of the line.

In order to moderate the peaks where demand would exceed supply, it is desirable to store the gas when the supply exceeds demand, whereby peaks in demand can be met from gas held in storage. For this purpose it is desirable to provide for the storage of gas in a liquefied state and to vaporize the liquid as demand requires. In another example, liquefaction of natural gas is useful in making possible the transport of gas from a source of plentiful supply to a distant market, particularly when the source of supply cannot be directly joined with the market by pipeline. This is particularly true where transport must be made by ocean going craft. Transportation of natural gas in the gaseous state would be uneconomical unless the natural gas was highly compressed, and then the system would not be economical because it would be impractical to provide containers of suitable strength and capacity.

In order to reduce natural gas to a liquefied state (i.e., liquefied natural gas or LNG) cooling is require to a temperature of about −240° F. to −260° F. (−151° C. to −162° C.) at atmospheric pressure. Numerous systems exist for the liquefaction of natural gas or the like in which the gas is liquefied by passing it sequentially through a plurality of cooling stages, to cool the gas to successively lower temperatures until the liquefaction temperature is reached. For example, cooling can be accomplished by indirect heat exchange with one or more expanded refrigerants such as propane, propylene, ethane, ethylene, and methane.

In general, gases, and specifically raw natural gas from a well, need to be processed before such gases can be liquefied. Such processing can include processing referred to as "sweetening," wherein hydrogen sulfide ($H_2S$) removal occurs and carbon dioxide ($CO_2$) removal occurs. Mercury (Hg) removal and moisture (water, $H_2O$) removal occur after "sweetening."

Dehydration is the removal of moisture content from the gas (i.e., natural gas). One example is that elevated moisture in natural gas conduit (e.g., LNG pipeline) can form methane-hydrate at high pressure and blocks conduit. Another example is that moisture condensation can corrode equipment. As yet another example is that elevated moisture can cause ice formation that can severely damage cryogenic equipment if the amount of ice is significant. Generally, moisture content in natural gas has to be reduced to below 1 ppm (part per million) before it can be cryogenically processed further.

Within a liquefaction system (e.g., a LNG plant) a moisture analyzer is usually provided to monitor the gas after a gas dehydration process is performed upon the gas but before a liquefaction process is preformed upon the gas. The purpose of the moisture analyzer is to monitor moisture content and make sure it is below a desired amount (e.g., 1 ppm) before the gas proceeds to the liquefaction process. When the moisture analyzer indicates moisture content higher than the desired amount (e.g., an action level amount), the cause can be from various sources. For example, the action-level indication can be a result of system leakage or a saturated dryer that is due for regeneration. Before any action is to be taken concerning remedying the cause of the action-level indication, sometimes it is useful to confirm that an action-level moisture indication by the moisture analyzer is correct. In other words, it is sometimes useful to check/test the operation of the moisture analyzer.

A moisture provision system may be used to provide a known moisture content to gas within a moisture provision and analyzer arrangement. One example of a moisture provision system can include a permeation tube with water provided therein. Such gas of known moisture content can then be supplied to the moisture analyzer. If the moisture indication (e.g., sensed reading) from the moisture analyzer for the known-moisture gas is within a certain tolerance of an expected indication, the moisture analyzer is deemed to be reliable. With the reliability of the moisture analyzer confirmed, investigation of other possible reasons for the action-level moisture indication can be logically pursued. For example, a technician can proceed to trouble-shoot for a possible leakage or a dryer could be in need of being switched-off to allow for regeneration. If the moisture indication from moisture analyzer for the known-moisture gas is not within the certain tolerance of the expected indication, the moisture analyzer and verification system can be re-examined carefully before any other action might be undertaken.

As can be appreciated, provision of the known moisture content to the gas and the supply of such known-moisture gas to the moisture analyzer is a selective process. In other words, such provision of known-moisture gas to the moisture analyzer is only performed at some, select times during overall operation of the liquefaction system (e.g., a LNG plant). Accordingly, the moisture provision and analyzer arrangement has components to selectively provide moisture to the gas and selectively supply the known-moisture gas to the moisture analyzer.

It should be appreciated that it may not be prudent to completely cease flow of gas through the moisture provision and analyzer arrangement when the moisture analyzer is selectively not operating to sense moisture content. If gas flow through the moisture provision and analyzer arrangement were to completely cease, is possible that moisture could start to accumulate within the moisture provision and analyzer arrangement. Such accumulation of moisture could adversely affect components of the moisture provision and analyzer arrangement. Also, such accumulation of moisture could adversely affect the operation/accuracy of the moisture analyzer within the arrangement. In one example, such moisture accumulation could occur in dead space(s) within/near the moisture provision and analyzer arrangement and when gas flow toward the moisture provision and analyzer arrangement is initiated/occurring, such moisture accumulation could the contaminate gas flow. The contamination would be in the form of added moisture above the level that is otherwise present in the gas.

In order to avoid undesirable moisture accumulation within/near the moisture provision and analyzer arrangement, another flow is utilized that proceeds through the arrangement but which does not proceed through the moisture analyzer. This other flow is referred to as a bypass flow because the flow is by-passing the moisture analyzer within the arrangement. One or more switching valves are provided within the moisture provision and analyzer arrangement for gas flow path selection of either a path through the moisture analyzer or the bypass.

It has been noted that during switching of gas flow path selection (i.e., through the moisture analyzer or the bypass) discontinuity of flow rate can occur. It has also been noted that discontinuity of flow rate can cause some disruption of the ability of the moisture analyzer to properly function and provide an accurate indication of perceived moisture. For example, the moisture provision system (e.g., a permeation tube) may provide an incorrect/inconsistent/fluctuating moisture level at/following switching of gas flow path selection (i.e., through the moisture analyzer or the bypass). As one specific example, an overshoot of moisture provision may occur. As a result, an extra amount of settling time may be needed before the moisture analyzer can make an accurate/reliable measurement. As such, there is a need for improvements in moisture provision and analyzer arrangements. There would be a technical advantage provided by such improvements in that operation time improvements would be obtained thus permitting improvements in a determination time frame concerning the flowing gas.

BRIEF DESCRIPTION OF THE INVENTION

The following summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

One aspect of the invention provides a moisture provision and analyzer arrangement for providing and analyzing moisture of a flowing stream of natural gas. The arrangement includes a conduit for obtaining a sample flow of natural gas from the flowing stream of natural gas. The arrangement includes a moisture analyzer that analyzes a moisture content of the sample flow provided to thereto. The arrangement includes a bypass flow conduit that extends in fluid parallel to the moisture analyzer that provides a flow path through the moisture provision and analyzer arrangement without passing through the moisture analyzer. The arrangement includes a main orifice in fluid communication within the moisture provision and analyzer arrangement and located upstream from the moisture analyzer. The sample flow provided to the moisture analyzer is provided to and proceeds through the main orifice. The arrangement includes a bypass orifice located along the bypass flow conduit. The main orifice is sized and the sample flow provided to the moisture analyzer via the main orifice is provided at a pressure from the main orifice such that the sample flow provided to the moisture analyzer is at a critical flow condition and the bypass orifice is sized and the bypass flow is provided at a pressure to the bypass orifice such that the bypass flow proceeding through the bypass orifice is at a critical flow condition. Components in the moisture provision and analyzer arrangement are selected such that the critical flow rate through the main orifice and the critical flow rate through the bypass orifice are equal.

Another aspect of the invention provides a method of providing and analyzing moisture of a flowing stream of natural gas with a moisture provision and analyzer arrangement. The method includes providing a conduit for obtaining a sample flow of natural gas from the flowing stream of natural gas. The method includes providing a moisture analyzer that analyzes a moisture content of the sample flow provided to thereto. The method includes providing a bypass flow conduit that extends in fluid parallel to the moisture analyzer that provides a flow path through the moisture provision and analyzer arrangement without passing through the moisture analyzer. The method includes providing a main orifice in fluid communication within the moisture provision and analyzer arrangement and located upstream from the moisture analyzer. The sample flow provided to the moisture analyzer is provided to and proceeds through the main orifice. The method includes providing a bypass orifice located along the bypass flow conduit. The method includes sizing the main orifice and providing the sample flow to the moisture analyzer via the main orifice at a pressure from the main orifice such that the sample flow provided to the moisture analyzer is at a critical flow condition. The method includes sizing the bypass orifice and providing the bypass flow at a pressure to the bypass orifice such that the bypass flow proceeding through the bypass orifice is at a critical flow condition. Components in the moisture provision and analyzer arrangement are selected such that the critical flow rate through the main orifice and the critical flow rate through the bypass orifice are equal.

BRIEF DESCRIPTION OF THE DRAWINGS

The foregoing and other aspects of the invention will become apparent to those skilled in the art to which the invention relates upon reading the following description with reference to the accompanying drawings, in which.

DETAILED DESCRIPTION OF THE INVENTION

Figure 1:
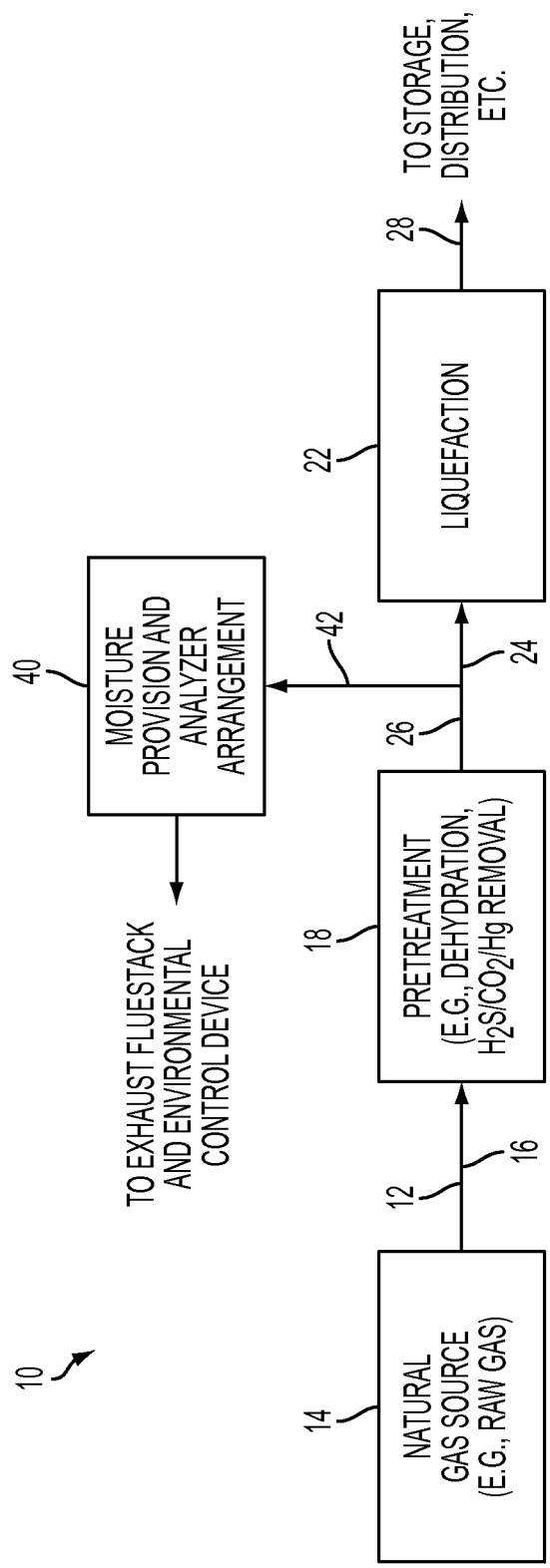
FIG. 1 is a schematic illustration of a liquefied natural gas processing system that includes a moisture provision and analyzer arrangement incorporating at least one aspect of the present invention.

Example embodiments that incorporate one or more aspects of the invention are described and illustrated in the drawings. These illustrated examples are not intended to be a limitation on the invention. For example, one or more aspects of the invention can be utilized in other embodiments and even other types of devices. Moreover, certain terminology is used herein for convenience only and is not to be taken as a limitation on the invention. Still further, in the drawings, the same reference numerals are employed for designating the same elements.

An example embodiment of a liquefied natural gas (LNG) processing system 10 that includes at least one aspect in accordance with the present invention is schematically shown within in FIG. 1. It is to be appreciated that the system 10 shown within FIG. 1 is simply one example and that other examples that include at least one aspect in accordance with the present invention are possible and contemplated.

Turning to the example of FIG. 1, untreated or "raw" natural gas 12 is provided from a source 14. Such a source may include one or more natural gas wells, pipe lines, holding facilities or the like. The specifics of the natural gas source need not be limitations upon the present invention.

The untreated natural gas 12 that is provided via the source 14 may contain one or more undesirable components. For example, hydrogen sulfide ($H_2S$), carbon dioxide ($CO_2$), mercury (Hg) and moisture (water $H_2O$) may be present within the untreated natural gas 12 provided from the natural gas source 14.

The natural gas source 14 is in fluid communication 16 with a pretreatment portion 18 of the system 10. The pretreatment portion 18 can provide for removal of at least some components from the untreated natural gas 12. For example, the pretreatment portion 18 may include structure(s) for the removal of moisture (e.g., dehydration) from the gas. Also, the pretreatment portion 18 may include structure for the removal of hydrogen sulfide, carbon dioxide and mercury.

Within the system 10, a liquefaction portion 22 is in fluid communication 24 downstream from the pretreatment portion 18 and pretreated natural gas 26 flows to the liquefaction portion. The liquefaction portion 22 may include any suitable structure for liquefying the pretreated natural gas 26 to provide liquefied natural gas (LNG) 28. Such structure may include portions for refrigerating (i.e., cooling) the natural gas, compressing the natural gas, and the like. Such structure may certainly be varied and thus need not be specific limitations upon the present invention. Subsequent to liquefaction, the LNG 28 may be provided to storage facilities, distribution or the like. Here also, such aspects need not be specific limitations upon the present invention.

As mentioned, dehydration is a process to remove moisture content from the gas, and specifically for this discussion, natural gas. Elevated moisture content within natural gas may pose concerns within the system 10. For example, moisture can block or clog conduits, pipe lines, and the like due. Also, such blockage/clogging can be associated with the formation of methane-hydrate at high pressure. Further, moisture condensation can cause corrosion within equipment of the system 10. Still further, significant ice formation during the liquefaction process could damage the equipment (e.g., cryogenic equipment within the liquefaction portion 22). In one general example, the moisture content within natural gas is to be typically reduced to below one part per million before it proceeds to the liquefaction portion 22. As such, there is need for the pretreatment to accomplish any need moisture removal so as to achieve the desired moisture content of below the example one part per million.

Within the system, a moisture provision and analyzer arrangement 40 is in fluid communication with the flow of pretreated gas 26 proceeding from the pretreatment portion 18 to the liquefaction portion 22. The moisture provision and analyzer arrangement 40 is so connected to permit at least some amount 42 (e.g., a sample amount) of the pretreated natural gas 26 to be diverted to the moisture provision and analyzer arrangement 40. This diversion of the sample amount 42 is subsequent to the pretreatment at the pretreatment portion 18 and prior to the pretreated gas reaching the liquefaction portion 22.

One purpose of the moisture provision and analyzer arrangement 40 is to monitor moisture content of the pretreated natural gas so as to ensure that the moisture content is below the desired amount (e.g., one part per million or the like) before the gas proceeds to liquefaction. In general, the analysis of moisture is to determine whether the system 10 may have one or more items that require attention. For example, there may be a leakage which permits undesired introduction of moisture into the flow of natural gas proceeding through the system 10. Also, it is possible that a component within the pretreatment portion 18 requires attention or service. For example, it is possible that the pretreatment portion includes one or more dryers which may become saturated with moisture removed from the natural gas. Such dryers may require service so as to regenerate the dryer to permit further use for moisture removal. Another purpose of the moisture provision and analyzer arrangement 40 is a moisture provision function. Provision of moisture allows moisture analyzer validation by providing a known moisture content (e.g., dry and wet) in the gas.

Figure 2:
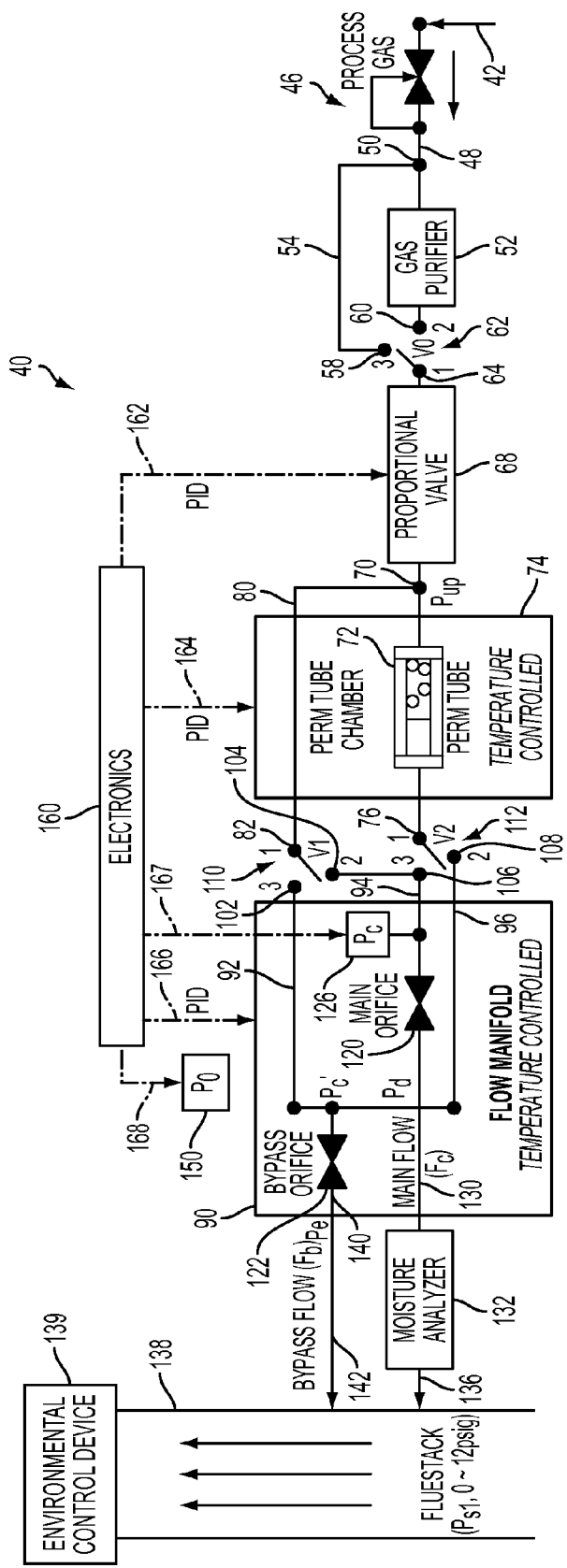
FIG. 2 is a schematic illustration of the moisture provision and analyzer arrangement of FIG. 1 and shows details in accordance with at least one aspect of the present invention.

FIG. 2 is a schematic illustration of one example of the moisture provision and analyzer arrangement 40 that includes at least one aspect in accordance with present invention. It is to be appreciated that only the small portion 42 of the overall pretreated natural gas 26 proceeds to the moisture provision and analyzer arrangement 40. The sample amount 42 is diverted from the majority of the flow of pretreated natural gas 26 (FIG. 1), which is otherwise proceeding toward the liquefaction portion 22. The sample amount 42 is for use (e.g., sampling/testing) by the moisture provision and analyzer arrangement 40 (FIG. 2).

Within the example moisture provision and analyzer arrangement 40, the gas proceeds first to a pressure regulator 46 which controls the pressure amount of the gas proceeding into the moisture provision and analyzer arrangement 40. The pressure regulator 46 is in fluid communication 48 with a junction point 50 and, in turn, in communication with a gas purifier 52. Also, from the junction point 50, a fluid communication line 54 extends to a bypass point 58 which bypasses the gas purifier 52. As such, the fluid communication line 54 is a bypass line.

Turning to the gas purifier 52, the gas purifier 52 can receive gas provided thereto proceeding from the pressure regulator 46. The gas purifier 52 operates to remove effectively all moisture from the gas proceeding there through. An output from the gas purifier 52 is a point 60. It is to be appreciated that the gas output from the gas purifier 52 effectively has a zero moisture point for use within the moisture provision and analyzer arrangement 40.

The moisture provision and analyzer arrangement 40 includes a valve (V0) 62 that is located downstream of the gas purifier 52 and the fluid communication (bypass) line 54. Specifically, the bypass point 58 and the output point 60 from the gas purifier 52 are two switch points within the valve (V0) 62. Specifically, the valve (V0) 62 has three points. Point 64 within the valve (V0) 62 is a common point "1," point 60 is a switch point "2" and bypass point 58 is a switch point "3." The valve (V0) 62 is operable between two states, with a first state being a connection from the common valve point (point 1) 64 to the switch point (point 2) 60 of the output of the gas purifier 52, and with a second state being a connection from the common valve point (point 1) 64 to the switch point (point 3) 58 of the of the bypass line 54.

Downstream from the valve (V0) $62_{in}$ the moisture provision and analyzer arrangement 40 includes a proportional valve 68. All flow of natural gas through the moisture provision and analyzer arrangement 40 proceeds through the proportional valve 68, irrespective of whether the gas proceeds through the gas purifier 52 or proceeds along the bypass line 54, and thus does not proceed through the gas purifier 52. The proportional valve 68 is configured and operational so as to provide a flow of natural gas through the main orifice with a constant pressure $P_c$ upstream of the main orifice.

Fluidly connected to the output of the proportional valve 68, at junction point 70, is a permeation tube 72, which is in turn within a permeation tube chamber 74. The permeation tube 72 is an encapsulated piece of tube, which can include a permeable material such as TEFLON®. Within the permeation tube 72 is provided a finite amount of water. This water can join with the natural gas flowing through the permeation tube 72 via passing through the permeable material. The permeation rate of water through the material to join with the natural gas is a function of the difference in water vapor pressure between the inside and outside of the tube, the tube surface area, tube wall thickness and the tube material permeability. Still further, permeability is a function of temperature of the permeation tube 72. The permeation tube chamber 74 provides for temperature control of the permeation tube 72.

It is to be appreciate that all the gas being supplied to the permeation tube 72 may initially have no moisture content (e.g., possibly having been removed by the gas purifier 52). Also, it is to be appreciated that the gas which proceeds through the permeation tube 72 can acquire some amount of moisture content. The acquired amount of moisture content can be a known controlled amount due to control of structural and operational aspects of the permeation tube 72. The output of the permeation tube extends to a point 76.

Returning to the output of the proportional valve 68 and thus the junction point 70, a second fluid communication line 80 extends from the junction point 70 and outside of the permeation tube 72. As such, the communication line 80 is a bypass line around the permeation tube 72 and can be referred to as a permeation tube bypass. The second, bypass line 80 extends to a point 82.

A flow manifold 90 is provided within the moisture provision and analyzer arrangement 40. The flow manifold 90 has three (first, second and third) inputs 92, 94, 96. The first manifold input 92 is in fluid connection with a point 102. The second manifold input 94 is in fluid connection with a point 104 and a point 106. The third manifold 96 is in fluid connection a point 108.

A valve 110 (V1) is provided within the moisture provision and analyzer arrangement 40 at the points 82, 102 and 104 and a valve 112 (V2) is provided at the points 76, 106 and 108. The valve 110 (V1) is a two position valve, with the point 82 being a common point identified within the drawings as "1." A first position of the valve 110 (V1) connects the common point 82 "1" to point 104 (identified within the drawings as "2") and a second position of the valve 110 (V1) connects the common point 82 "1" to point 102 (identified within the drawings as "3"). Thus, in the first position the valve 110 (V1) connects the bypass line 80 to the second manifold input 94, and in the second position the valve 110 (V1) connects the bypass line 80 to the first manifold input 92.

The valve 112 (V2) is a two position valve, with the point 76 being a common point identified within the drawings as "1." A first position of the valve 112 (V2) connects the common point 76 "1" to point 108 (identified within the drawings as "2") and a second position of the valve 112 (V2) connects the common point 76 "1" to point 106 (identified within the drawings as "3"). Thus, in the first position the valve 112 (V2) connects the permeation tube 72 to the third manifold input 96, and in the second position the valve 112 (V2) connects the permeation tube 72 to the second manifold input 94.

Within the flow manifold 90 two orifices 120, 122 are provided. Specifically, a first or main orifice 120 and a second/bypass orifice 122 are provided. The main orifice 120 has an input connected to the second input 94 of the flow manifold. Also at the input to the main orifice 120 and thus at the second input 94 to the flow manifold 90, a pressure sensor 126 for detecting a pressure $P_c$ is provided. The pressure $P_c$ is thus the pressure at the input to the main orifice 120. The first and third inputs 92 and 96 of the flow manifold 90 are in fluid connection to an input of the bypass orifice 122 within the flow manifold 90.

As can be appreciated via the connections of the manifold inputs 92-96 to the main and bypass orifices 120 and 122, the valve 112 (V2) is operable to connect the output of the permeation tube 72 to either the main orifice 120 or the bypass orifice 122. Similarly, the valve 110 (V1) is operative to connect the bypass line 80 proceeding around the permeation tube 72 to either the main orifice 120 or the bypass orifice 122.

The main orifice 120 has an output that proceeds, via a first output 130 of the flow manifold 90, to a moisture analyzer 132 of the moisture provision and analyzer arrangement 40. Flow from the main orifice 120 can be termed a main flow ($F_c$) and the main flow $F_c$ has a pressure $P_d$. The moisture analyzer 132 contains structure for determining the amount of moisture that is present within the gas flow (i.e., the main flow ($F_c$)) provided to the moisture analyzer.

An output 136 of the moisture analyzer 132 is in fluid connection to an exhaust flue stack 138. The exhaust flue stack 138 carries gases and that like that have been utilized, consumed or otherwise no longer needed. As such the gas proceeding through the moisture analyzer 132 is carried, possibly with other gas flow, out and away from the moisture provision and analyzer arrangement 40. It is to be appreciated that gas proceeding through the output 136 to the flue stack 138 is a very small amount in comparison to the other gases flowing within the flue stack. The exhaust flue stack 138 may be connected to further processing components, such as an environmental control device 139, ambient atmosphere, or the like. It is to be appreciated that the environmental control device 139 may include components to burn content proceeding within the flue stack 138 as flare gas or otherwise process the content proceeding within the flue stack. A pressure $P_{S1}$ within the exhaust flue stack 138 can be relatively low. In one example, the pressure $P_{S1}$ within the exhaust flue stack 138 is within the range of 0-12 psig.

The bypass orifice 122 is in fluid communication, via a second output 140 from the flow manifold 90, to a bypass flow line 142, which proceeds out from the moisture provision and analyzer arrangement 40. The bypass flow line 142 carries a bypass flow $F_b$ that has a pressure $P_e$. The bypass flow line 142 is in fluid connection with the exhaust flue stack 138 such that the bypass flow $F_b$ proceeding from the bypass orifice 122 is directed to the exhaust flue stack 138. As such the gas proceeding through the bypass orifice 122 is also carried, possibly with other gas flow, out and away from the moisture provision and analyzer arrangement 40. It is to be appreciated that gas proceeding through the bypass flow line 142 to the flue stack 138 is a very small amount in comparison to the other gases flowing within the flue stack. Again, it is to be recalled that the exhaust flue stack 138 may be connected to further processing components, such as an environmental control device 139, and that the environmental control device may include components to burn content proceeding within the flue stack 138 as flare gas or otherwise process the content proceeding within the flue stack.

The moisture provision and analyzer arrangement includes a pressure sensor 150 for determining an ambient pressure $P_0$ within the moisture provision and analyzer arrangement 40. Also, it is to be appreciated that a series of electronics 160 is operatively connected 162 to the proportional valve 68, operatively connected 164 to the permeation tube chamber 74, operatively connected 166 to the flow manifold 90, operatively connected 167 to the pressure sensor 126 and operatively connected 168 to the ambient pressure sensor 150.

Focusing upon the operative connection 162 of the electronics 160 to the proportional valve 68, the connection may provide for a proportional, integral and differential (PID) connection and control of the proportional valve 68 such that $P_c$, pressure upstream of main orifice is constant. This ensures that critical flow rate through the main orifice is always constant. Also, in general, the control is such that the pressure of the gas proceeding through the moisture provision and analyzer arrangement 40 can be controlled.

Turning to the operational connection 164 of the electronics 160 to the permeation tube chamber 74, the connection may provide for a PID connection. The permeation tube chamber 74 is configured so that temperature of the permeation tube chamber can be controlled. This control of temperature within the permeation tube chamber 74 thus allows maintenance of a desired temperature for the permeation tube. As mentioned, permeation of moisture at the permeation tube 72 is a function of temperature. Thus, temperature of the permeation tube is controlled so that moisture transmission through the permeation tube is at a desired rate.

The operative connection 166 between the electronics 160 and the flow manifold 90 temperature control maybe provided as a PID connection. As mentioned, the electronics 160 are operatively connected 168 to the ambient pressure sensor 150. The ambient pressure $P_0$ derived from the ambient pressure sensor 150 and the pressure $P_c$ from the sensor 126, via connection 167 at the input of the main orifice 120 are used to determine critical flow rate through the main orifice.

Turing to the operation of the moisture provision and analyzer arrangement 40, the arrangement can operate in three different modes. These modes are referred to as (1) process mode, (2) dry mode and (3) wet mode. The operation of the moisture provision and analyzer arrangement 40 is dependent upon the positioning of the three valves 62, 110 and 112 (V0-V2). The operational positions of the three valves 62, 110 and 112 (V0-V2) for the three operational modes is presented within the following Table 1.

TABLE 1

| Operating Modes | | | |
| --- | --- | --- | --- |
| | V0 | V1 | V2 |
| Process Mode | 1-3 | 1-2 | 1-2 |
| Dry Mode | 1-2 | 1-2 | 1-2 |
| Wet Mode | 1-2 | 1-3 | 1-3 |

Within the process mode, a gas sampling that would otherwise proceed from the pretreatment portion 18 of the system (see FIG. 1) to the liquefaction portion 22 is to be analyzed or tested to determine moisture content. For such process mode, the valve 62 (V0) in FIG. 2 is in a connection between points 64 and 58 (position 1-3) such that the gas does not proceed through the gas purifier 52 but instead proceeds along the bypass line 54 around the gas purifier. The gas then proceeds through the proportional valve 68 and to the junction point 70 upstream of the permeation tube 72. The gas can proceed through the permeation tube 72. However, for the process mode, the valve 112 (V2) is in a connection between points 76 and 108 (position 1-2) so that output of the permeation tube 72 is in fluid connection with the input of the bypass orifice 122 within the flow manifold 90. Accordingly, such gas is directed to the bypass orifice 122. In due course, such gas proceeds through the bypass orifice 122 and is directed to the flue stack 138. It is to be appreciated that moisture may be added to such gas proceeding through the permeation tube 72 and through the bypass orifice 122. However, such moisture addition is not of consequence to operation. The gas is merely presented to the flue stack 138 without monitoring of the moisture content.

Returning to the junction point 70 upstream of the permeation tube 72, it should be appreciated that gas also flows along the permeation tube bypass line 80 to the valve 110 (V1). Within the process mode, the valve 110 (V1) is in the position 1-2 (connection between point 82 and point 104) so that the bypass line 80 around the permeation tube 72 is in fluid connection with the second input 94 of the flow manifold 90 and thus is in fluid connection to the input of the main orifice 120 within the flow manifold. Accordingly, such gas can proceed through the main orifice 120 and to the moisture analyzer 132. Such gas being analyzed by the moisture analyzer is a sample of the bulk of the pretreated natural gas 26 proceeding from the pretreatment portion 18 (FIG. 1) of the system 10 to the liquefaction portion 22 of the system. Thus, the actual moisture content of the pretreated natural gas 26 proceeding to the liquefaction portion 22 is monitored.

The moisture provision and analyzer arrangement 40 (FIG. 2) provides for an ability to verify/confirm that the moisture analyzer 132 is correctly analyzing/determining the moisture content. In order to make such verification, the moisture provision and analyzer arrangement 40 will proceed through the dry mode and then subsequently through the wet mode. Within the dry mode, the valve 62 (V0) is in the position 1-2 (points 64 and 60 are connected). As such, the bypass line 54 around the gas purifier 52 is disconnected and gas proceeds through the gas purifier for removal of moisture and the like. Also within the dry mode, the valve 110 (V1) is in the position 1-2 (points 82 and 104 are connected) such that gas proceeding from the proportional valve 68, which has been dried via the gas purifier 52 can proceed around the permeation tube via the bypass line 80 and to the main orifice 120. This allows for dried gas to proceed through the main orifice 120 and through the moisture analyzer 132. The flow of such dried gas dries this series of lines and the components thereon. The valve 112 (V2) is in the position 1-2 (points 76 and 108 are connected) such that gas flowing through the permeation tube 72 is directed to the input of the bypass orifice 122 and subsequently to the flue stack 138. Moisture may have been added to such gas via the permeation tube 72. However, such is not of consequence during operation within the dry mode.

As mentioned, the verification eventually requires the operation of the moisture provision and analyzer arrangement 40 within the wet mode. Within the wet mode, the valve 62 (V0) is retained within the position 1-2 (points 64 and 60 are connected) such that the bypass line 54 around the gas purifier 52 is disconnected and the gas proceeds only through the gas purifier to be dried (e.g., moisture removed) and the like. Again the gas proceeds through the proportional valve 68 and to the junction point 70 upstream of the permeation tube 72. The valve 112 (V2) is in the position 1-3 (points 76 and 106 are connected) so that gas proceeding through the permeation tube 72 is connected to the input to the main orifice 120. It is to be appreciated that within the permeation tube 72, moisture can be added to the flow of gas proceeding there through. As such, the gas proceeding from the main orifice 120 to the moisture analyzer 132 has moisture (e.g., moister laden). The amount of moisture that is introduced or added into the gas by the permeation tube 72 is controlled. Specifically, the moisture introduction is a known amount such that there expectation as to the moisture content that the moisture analyzer 132 will discern. Such can be utilized as a check to determine the proper operation of the moisture analyzer 132. Specifically, if the moisture analyzer 132 provides an indication of discerned moisture content that is generally equal to the controlled, know amount of moisture that was introduced by the permeation tube, the moisture analyzer 132 and the system 10 as a whole can be deems to be operating properly. However, if the moisture analyzer 132 provides an indication of discerned moisture content that is generally not equal to the controlled, know amount of moisture that was introduced by the permeation tube, such provides an indication that some portion or aspect of the moisture provision and analyzer arrangement 40 may not be operating properly.

Also within the wet mode, the valve V1 is in the connection 1-3 (points 82 and 102 are connected together). As such, flow proceeding along the bypass line 80 around the permeation tube 72 is connected to the input of the bypass orifice 122 and subsequently to the flue stack 138. This maintained flow provides some benefit as discussed below.

It should be appreciated that both the main orifice 120 and the bypass orifice 122 provide a certain amount of restriction or resistant to flow of gas proceeding respectively there through. It should be appreciated that the need for the bypass flow, which bypasses the moisture analyzer 132, within the moisture provision and analyzer arrangement 40 is beneficial to maintain at least some flow constantly through the moisture provision and analyzer arrangement 40. Such constant flow can help to keep the moisture provision and analyzer arrangement 40 dry and thus prevent unwanted accumulation of moisture. Without a bypass flow, moisture could start to accumulate in still space(s) and contaminate flow within the moisture provision and analyzer arrangement 40 when it is desired to perform an analysis of moisture via the moisture analyzer 132.

Turing to specifics of operation of the moisture provision and analyzer arrangement 40, moisture introduced at permeation tube 72 provides a moisture content that can be defined by:

$$H_{ppm} = \frac{\frac{P_r}{MW_{H2O}}}{\frac{P_r}{MW_{H2O}} + \frac{P_0 \cdot F_c}{R_0 \cdot T_0}} \quad \text{Equation 1}$$

where: $P_r$ is water emission rate (ngm/min) at a certain temperature;
  $MW_{H2O}$ is water molecular weight (gm/mol)
  $P_0$ is ambient, standard pressure (pa)—usually at 1 atmospheric pressure
  $T_0$ is standard temperature (K)—usually at 25 C
  $R_0$ is universal gas constant—8.31 J/(mol*K)
  $F_c$ is mass flow rate (standard cc per minute) at $P_0$ and $T_0$
As mentioned, maintaining the permeation tube 72 at a constant temperature helps to keep the water emission rate ($P_r$) constant.

Within the wet mode, gas through main orifice is $F_c$ and is called main flow ($F_c$). Gas through bypass orifice is called bypass flow ($F_b$). As mentioned, the main flow ($F_c$) is analyzed by the moisture analyzer 132 before being vented to the flue stack 138. Bypass flow ($F_b$) is gas flow through the rest of verification system to keep it dry. Without bypass flow, moisture would start to accumulate in dead space and contaminate main flow.

In accordance with one aspect of the present invention, it has been discovered that it is beneficial to maintain/control the bypass flow $F_b$ rate to be as close to main flow $F_c$ rate as possible. Otherwise, main flow rate $F_c$ may experience discontinuity when verification operating mode is changed if $F_b$ does not substantially equal (i.e., ≠) $F_c$. As a result, the main flow $F_c$ might need an additional/extra amount of time to settle before moisture analyzer 132 can make a reliable measurement. Secondly, if $F_b \neq F_c$, when operating mode changes from dry mode to wet mode, overshoot in moisture may be observed from the moisture analyzer 132 due to different flow rates through permeation tube during dry mode and wet mode. Thirdly, moisture introduction by the permeation tube 72 may become unstable when operating mode changes from dry mode to wet mode if $F_b \neq F_c$. The temperature for the permeation tube 72 and temperature of the flow manifold 90 become constant only when gas flow Fb and Fc are stable. This is due to the fact that ambient temperature may change (e.g., from −20 C to 50 C) and gas temperature is affected by this change in temperature. If gas flow is always stable and constant inside permeation tube 72 and flow manifold 90, a thermal equilibrium is reached after an initial, relatively short transient period. However, if gas flow $F_b \neq F_c$ and flow becomes unstable when operating mode switches from dry mode to wet mode, permeation tube temperature and flow manifold temperature will become unstable. Overshoot in moisture introduction by the permeation tube 72 may occur and it will take additional/extra time for moisture to be stable at the expense of response time.

One aspect of the present invention is to employ a critical flow concept to maintain main flow Fc and bypass flow $F_b$ equal and constant. It is to be appreciated that critical flow occurs at an orifice if the upstream absolute pressure is at least 1.98 times of downstream absolute pressure. For main flow, if $$\frac{P_c}{P_d} > \left(\frac{k+1}{2}\right)^{\frac{k}{k-1}},$$

flow through main orifice becomes critical and its flow rate is expressed as:

$$Fc = Cr_c \cdot A \cdot \frac{T_{ref}}{P_{ref}} \cdot \frac{P_c + P_0}{\sqrt{T}} \cdot \sqrt{\frac{k \cdot R_0}{MW} \cdot \left(\frac{2}{k+1}\right)^{\frac{k+1}{k-1}}} \quad \text{Equation 2}$$

where: $Cr_c$: flow coefficient for main flow
  $A_c$: area of cross section for main flow orifice
  $T_{ref}$: reference temperature in K, usually 273.15K
  $P_{ref}$: reference pressure in Pascal, usually 1.013e+5 Pa
  $P_C$: main flow orifice upstream pressure (Pa)
  $P_0$: ambient pressure (Pa)
  T: flow manifold orifice temperature (K)
  k: specific heat of gas (1.4 for most gases)
  $R_0$: universal gas constant (8.31 J/mol*K)
  MW: gas' molecular weight When main flow becomes critical, mass flow rate Fc is independent of downstream pressure condition. Flue stack back pressure may fluctuate between 0~10 psig. If critical flow condition is not met, main flow rate will vary with flue stack back pressure fluctuations. However, if critical flow condition is met, main flow rate (Fc) becomes constant as long as upstream pressure Pc is stable. Such stability is shown via the bypass flow $F_b$ becomes critical if:

$$\frac{P'_c}{P_e} > \left(\frac{k+1}{2}\right)^{\frac{k}{k-1}}$$

$$F_b = Cr_b \cdot A_b \cdot \frac{T_{ref}}{P_{ref}} \cdot \frac{P'_c + P_0}{\sqrt{T}} \cdot \sqrt{\frac{k \cdot R_0}{MW} \cdot \left(\frac{2}{k+1}\right)^{\frac{k+1}{k-1}}} \quad \text{Equation 3}$$

where: $Cr_b$: flow coefficient for bypass flow
$A_b$: area of cross section for bypass flow orifice
Pc': bypass flow orifice upstream pressure (Pa)
Pressure drop across V1 is denoted as DPV1. Pressure drop across V2 is denoted as DPV2. Pressure drop across the perm tube is denoted as DPPT. Pc and Pc' are related through the following relationship:

$$P_c = P_{up} - DP_{PT} - DP_{V2} \quad \text{Equation 4:}$$

$$P_c' = P_{up} - DP_{V1} \quad \text{Equation 5:}$$

In one example, V1 and V2 can be general-purpose 3-way solenoid valves. The orifice inside V1 and V2 can be very large so that their pressure drops are minimal, i.e., DPV1=DPV20. In other words, the valves V1 and V2 cause negligible pressure drops for flow therethrough. Also, within one example, the permeation tube chamber 74 is a stainless steel housing with the permeation tube 72 inside. In such an example, there is no flow restriction inside the chamber 74, so its pressure drop, DPPT is considered to be negligible. As such, the pressure upstream of the main orifice and pressure upstream of the bypass orifice are equal. Thus:

$$P_c = P_c' \quad \text{Equation 6:}$$

The main orifice 120 and bypass orifice 122 are identical in structure and size within tolerance, so:

$$Cr_c = Cr_b \quad \text{Equation 7:}$$

$$A_c = A_b \quad \text{Equation 8:}$$

Accordingly (see Equations 2-8):

$$Fc = Fb \quad \text{Equation 9:}$$

Once Fc and Fb become critical and Fc=Fb, they become stable even if their orifice downstream pressures fluctuate, as long as their orifice upstream pressure Pc and flow manifold temperature T are stable. Pc is electronically controlled by the upstream proportional valve. Flow manifold temperature T is controlled electronically. Fc and Fb may vary due to change in gas molecular weight if gas compositions vary.

As such, one aspect of the present invention is to apply the above-discussed critical flow principle in conjunction with use two critical orifices to allow equal amount of gas flow simultaneously through permeation tube 72 and the rest of the moisture provision and analyzer arrangement 40. In one example aspect, the main orifice 120 is sized and the sample flow provided to the moisture analyzer 132 via the main orifice is provided at a pressure from the main orifice such that the sample flow provided to the moisture analyzer is at a critical flow condition and the bypass orifice 140 is sized and the bypass flow is provided at a pressure to the bypass orifice such that the bypass flow proceeding through the bypass orifice is at a critical flow condition. One possible benefit in accordance with an aspect of the present invention is an ability to output process gas, dry gas and wet gas at a constant stable flow rate regardless downstream back pressure fluctuation. The critical flow condition through the main orifice and the critical flow condition through the bypass orifice are not affected by the variable pressure within the flue stack. It may be appreciated that natural gas has a dominant gas composition of methane, so the present invention may be particularly useful for applicable to natural gas.

The invention has been described with reference to the example embodiments described above. Modifications and alterations will occur to others upon a reading and understanding of this specification. Example embodiments incorporating one or more aspects of the invention are intended to include all such modifications and alterations insofar as they come within the scope of the appended claims.

What is claimed is:

1. A moisture provision and analyzer arrangement for providing and analyzing moisture of a flowing stream of natural gas, the arrangement including: a conduit for obtaining a sample flow of natural gas from the flowing stream of natural gas; a moisture analyzer that analyzes a moisture content of the sample flow provided to thereto; a bypass flow conduit that has a fluid flow path that is parallel to a fluid flow path of the moisture analyzer and that provides a flow path through the moisture provision and analyzer arrangement without passing through the moisture analyzer; a main orifice in fluid communication within the moisture analyzer and located upstream from the moisture analyzer, the sample flow provided to the moisture analyzer is provided to and proceeds through the main orifice; and a bypass orifice located along the bypass flow conduit, with flow proceeding along the bypass flow conduit proceeding through the bypass orifice; the main orifice is sized and the sample flow provided to the moisture analyzer via the main orifice is provided at a pressure from the main orifice such that the sample flow provided to the moisture analyzer is at a critical flow condition, with an absolute pressure upstream of the main orifice being at least 1.98 times an absolute pressure downstream of the main orifice, and the bypass orifice is sized and the bypass flow is provided at a pressure to the bypass orifice such that the bypass flow proceeding through the bypass orifice is at a critical flow condition, with an absolute pressure upstream of the bypass orifice being at least 1.98 times an absolute pressure downstream of the bypass orifice.

2. A moisture provision and analyzer arrangement for providing and analyzing moisture of a flowing stream of natural gas the arrangement including: a conduit for obtaining a sample flow of natural gas from the flowing stream of natural gas, a moisture analyzer that analyzes a moisture content of the sample flow provided to thereto; a bypass flow conduit that has a fluid flow path that is parallel to a fluid flow path of the moisture analyzer and that provides a flow path through the moisture provision and analyzer arrangement without passing through the moisture analyzer; a main orifice in fluid communication within the moisture analyzer and located upstream from the moisture analyzer, the sample flow provided to the moisture analyzer is provided to and proceeds through the main orifice; a bypass orifice located along the bypass flow conduit, with flow proceeding along the bypass flow conduit proceeding through the bypass orifice; a gas purifier for removing moisture from the sample flow of natural gas; a bypass line extending around the gas purifier; and a first valve for selecting a flow path through either the gas purifier or the bypass line; the main orifice is sized and the sample flow provided to the moisture analyzer via the main orifice is provided at a pressure from the main orifice such that the sample flow provided to the moisture analyzer is at a critical flow condition and the bypass orifice is sized and the bypass flow is provided at a pressure to the bypass orifice such that the bypass flow proceeding through the bypass orifice is at a critical flow condition.

3. The moisture provision and analyzer arrangement as set forth claim 2, including a permeation tube for introducing moisture to at least some of the sample flow of natural gas to provide a moister laden gas, a permeation tube bypass line extending around the permeation tube for flow of natural gas that does not receive moisture introduction, and second and third valves for selectively connecting the permeation tube to one of the main orifice and the bypass orifice and selectively connecting the permeation tube bypass line to the other of the main orifice and the bypass orifice.

4. The moisture provision and analyzer arrangement as set forth claim 3, wherein the first-third valves are operative to provide a process mode, a dry mode and a wet mode within the moisture provision and analyzer arrangement.

5. The moisture provision and analyzer arrangement as set forth claim 4, wherein within the process mode the obtained sample flow of natural gas from the flowing stream of natural gas is directed by the first valve along the bypass line extending around the gas purifier, by the second valve, via the bypass line extending around the permeation tube, to the main orifice and the moisture analyzer.

6. The moisture provision and analyzer arrangement as set forth claim 5, wherein within the process mode the third valve directs gas proceeding from the permeation tube to the bypass orifice.

7. The moisture provision and analyzer arrangement as set forth claim 4, wherein within the dry mode the obtained sample flow of natural gas from the flowing stream of natural gas is directed by the first valve through the gas purifier, by the second valve, via the bypass line extending around the permeation tube, to the main orifice and the moisture analyzer.

8. The moisture provision and analyzer arrangement as set forth claim 7, wherein within the dry mode the third valve directs gas proceeding from the permeation tube to the bypass orifice.

9. The moisture provision and analyzer arrangement as set forth claim 4, wherein within the wet mode the obtained sample flow of natural gas from the flowing stream of natural gas is directed by the first valve through the gas purifier, by the third valve, via the permeation tube, to the main orifice and the moisture analyzer.

10. The moisture provision and analyzer arrangement as set forth claim 9, wherein within the wet mode the second valve directs gas proceeding from the bypass line extending around the permeation tube to the bypass orifice.

11. The moisture provision and analyzer arrangement as set forth claim 3, wherein the second valve causes a negligible drop for flow therethrough, and the third valve causes a negligible drop for flow therethrough, the permeation tube chamber causes a negligible drop for flow therethrough, such that a pressure upstream of the main orifice and pressure upstream of the bypass orifice are equal.

12. The moisture provision and analyzer arrangement as set forth claim 1, wherein the moisture analyzer and the bypass orifice direct outflow to a flue stack that has a variable pressure, the critical flow condition through the main orifice and the critical flow condition through the bypass orifice are not affected by the variable pressure within the flue stack.

13. A method of providing and analyzing moisture of a flowing stream of natural gas with a moisture provision and analyzer arrangement, the method including: providing a conduit for obtaining a sample flow of natural gas from the flowing stream of natural gas; providing a moisture analyzer that analyzes a moisture content of the sample flow provided to thereto; providing a bypass flow conduit that has a fluid flow path that is parallel to a fluid flow path of the moisture analyzer that provides a flow path through the moisture provision and analyzer arrangement without passing through the moisture analyzer; providing a main orifice in fluid communication within the moisture analyzer and located upstream from the moisture analyzer, the sample flow provided to the moisture analyzer is provided to and proceeds through the main orifice; providing a bypass orifice located along the bypass flow conduit, with flow proceeding along the bypass flow conduit proceeding through the bypass orifice; sizing the main orifice and providing the sample flow to the moisture analyzer via the main orifice at a pressure from the main orifice such that the sample flow provided to the moisture analyzer is at a critical flow condition, with an absolute pressure upstream of the main orifice being at least 1.98 times an absolute pressure downstream of the main orifice; and sizing the bypass orifice and providing the bypass flow at a pressure to the bypass orifice such that the bypass flow proceeding through the bypass orifice is at a critical flow conditions with an absolute pressure upstream of the bypass orifice being at least 1.98 times an absolute pressure downstream of the bypass orifice.

14. The method set forth claim 13, including providing a gas purifier for removing moisture from the sample flow of natural gas, a bypass line extending around the gas purifier and a first valve for selecting a flow path through either the gas purifier or the bypass line, and selectively operating the first valve.

15. The method as set forth claim 13, including providing a permeation tube for introducing moisture to at least some of the sample flow of natural gas to provide a moister laden gas, providing a permeation tube bypass line extending around the permeation tube for flow of natural gas that does not receive moisture introduction, and providing second and third valves for selectively connecting the permeation tube to one of the main orifice and the bypass orifice and selectively connecting the permeation tube bypass line to the other of the main orifice and the bypass orifice, and selectively operating the second and third valves.

16. The method as set forth claim 14, wherein the steps of selectively operating the first valve and selectively operating the second and third valves provide a process mode, a dry mode and a wet mode within the moisture provision and analyzer arrangement.

17. The method as set forth claim 15, wherein within the process mode the obtained sample flow of natural gas from the flowing stream of natural gas is directed by the first valve along the bypass line extending around the gas purifier, by the second valve, via the bypass line extending around the permeation tube, to the main orifice and the moisture analyzer, and the third valve directs gas proceeding from the permeation tube to the bypass orifice.

18. The method as set forth claim 15, wherein within the dry mode the obtained sample flow of natural gas from the flowing stream of natural gas is directed by the first through the gas purifier, by the second valve, via the bypass line extending around the permeation tube, to the main orifice and the moisture analyzer, and the third valve directs gas proceeding from the permeation tube to the bypass orifice.

19. The method as set forth claim 15, wherein within the wet mode the obtained sample flow of natural gas from the flowing stream of natural gas is directed by the first through the gas purifier, by the third valve, via the permeation tube, to the main orifice and the moisture analyzer, and the second valve directs gas proceeding from the bypass line extending around the permeation tube to the bypass orifice.

20. The method as set forth claim 13, wherein the moisture analyzer and the bypass orifice direct outflow to a flue stack that has a variable pressure, the critical flow condition through the main orifice and the critical flow condition through the bypass orifice are not affected by the variable pressure within the flue stack.

* * * * *